United States Patent [19]

Fang

[11] Patent Number: 4,989,604
[45] Date of Patent: Feb. 5, 1991

[54] ELECTROMAGNETIC DEVICE

[75] Inventor: Paul Y. Fang, Anaheim, Calif.

[73] Assignee: ACCU Science Corporation, Orange, Calif.

[21] Appl. No.: 783,477

[22] Filed: Oct. 3, 1985

[51] Int. Cl.$^5$ .............................................. A61N 1/40
[52] U.S. Cl. .................................. 128/421; 128/907; 600/14
[58] Field of Search ........ 128/419 PG, 420 A, 420 R, 128/421, 422, 799, 1.4, 1.5

[56] References Cited

U.S. PATENT DOCUMENTS

| | | | |
|---|---|---|---|
| 1,120,964 | 12/1914 | Neel | 128/1.5 |
| 1,624,397 | 4/1927 | Dequer | 128/1.5 |
| 3,881,495 | 5/1975 | Pannozzo et al. | 128/422 |
| 3,897,789 | 8/1975 | Blanchard | 128/422 |
| 3,900,020 | 8/1975 | Lock | 128/422 |
| 3,908,669 | 9/1975 | Man et al. | 128/422 |
| 3,946,745 | 3/1976 | Hsiang-Lai et al. | 128/422 |
| 4,055,190 | 10/1977 | Tany | 128/422 |
| 4,056,097 | 11/1977 | Maass | 128/1.5 |
| 4,262,672 | 4/1981 | Kief | 128/422 |
| 4,349,030 | 9/1982 | Belgard et al. | 128/429 PG |
| 4,454,883 | 6/1984 | Fellus | 128/1.5 |

FOREIGN PATENT DOCUMENTS

| | | | |
|---|---|---|---|
| 5663 | 11/1979 | European Pat. Off. | 128/1.5 |
| 2634401 | 7/1976 | Fed. Rep. of Germany | 128/422 |
| 2736345 | 2/1979 | Fed. Rep. of Germany | 128/1.5 |
| 574068 | 12/1981 | U.S.S.R. | 128/419 R |
| 1162443 | 6/1985 | U.S.S.R. | 128/1.5 |

OTHER PUBLICATIONS

"The Fundamentals of Physics", by Halliday et al.; John Wiley & Sons, New York, 1974; p. 584.

Primary Examiner—William E. Kamm
Assistant Examiner—David Shay
Attorney, Agent, or Firm—Blakely, Sokoloff, Taylor, Zafman

[57] ABSTRACT

An electromagnetic energy pulse emitter is disclosed for applying electromagnetic pulses in the frequency range of 2 to 16 hertz to acupuncture points on a patient. The device comprises a transformer and an oscillator for producing electrical pulses of the appropriate frequency and a pair of transducers to produce an electromagnetic pulse responsive to the electrical pulses. Each transducer comprises a primary coil and a secondary coil electrically connected in series thereto, and aligned therewith along the central axis thereof to produce a relatively linear pulse directed along the axis thereof.

2 Claims, 2 Drawing Sheets

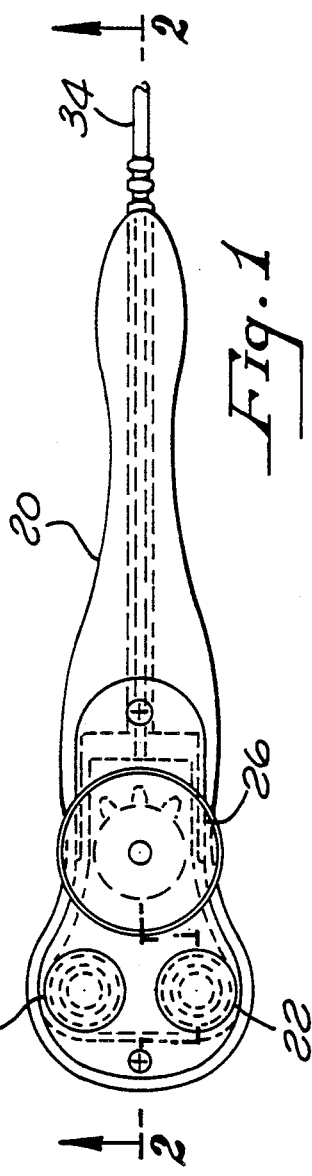
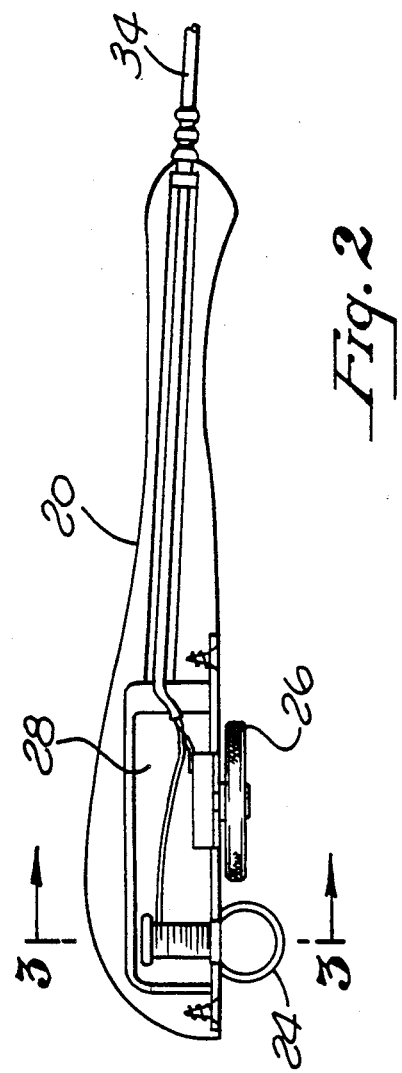
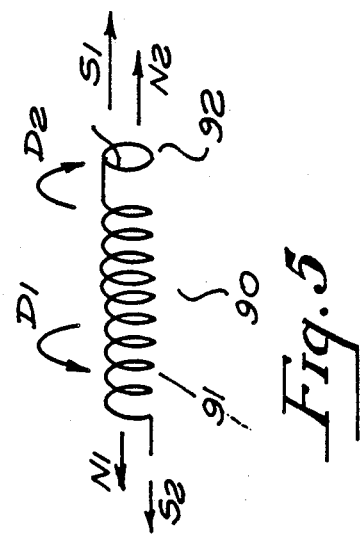
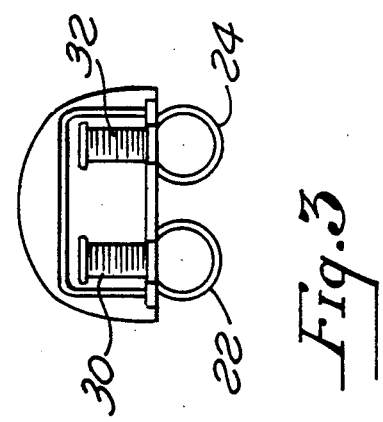

ELECTROMAGNETIC DEVICE

FIELD OF THE INVENTION

The present invention relates generally to an acupuncture device, and more particularly, to an apparatus for generating electromagnetic pulses for application to acupuncture points on a body and the method for performing the same.

BACKGROUND OF THE PRIOR ART

The science of acupuncture has been practiced in China for many centuries. However, only recently has it attracted the interest of the western world, and thus, only recently has it been exposed to the scientific methods of the west.

As originally practiced, acupuncture treatment required that acupuncture needles comprising thin stainless steel needles approximately 5 inches long, be inserted into a patient's body at very precise points, called acupuncture points, or trigger points, for stimulating certain nerve lines called meridians. Different symptoms can be treated by selectively stimulating specific acupuncture points.

Although it is known that the Chinese have used electricity as a means of stimulation of the acupuncture points, in addition to simply inserting acupuncture needles in the proper sites, little is known about the early Chinese electrical stimulators, since there appears to be no publications on the subject, and further, it has been extremely difficult to remove such devices from China up to the present time. However, from the limited information available, it is known that the Chinese electrical devices primarily use a d.c. current source which has a tendency to electrically shock the patient. Moreover, because of the Chinese intuitive approach to acupuncture treatment, no metering systems have been used in conjunction with the equipment.

With the recent interest in acupuncture treatment in the west, a few electrical devices for acupuncture have appeared in the western markets. Most of such devices such as that disclosed in Lock, U.S. Pat. No. 3,900,020, Blanchard, U.S. Pat. No. 3,897,789, McCall, U.S. Pat. No. 4,319,584, Eugenio, U.S. Pat. No. 4,052,978 and Wing, U.S. Pat. No. 4,180,079, all relate to instruments for acupuncture treatment in which actual low level electric current is directly applied, continuously or in pulse form, to a patient, particularly at acupuncture points on a patient's body.

A number of other patents, such as Brown, U.S. Pat. No. 435,376, Neel, U.S. Pat. No. 1,120,964, Elmi, U.S. Pat. No. 3,337,776 and Gorden et al, U.S. Pat. No. 3,664,327 disclose, the general application of electromagnetic radiation to a body for various medical purposes. MacLean, U.S. Pat. No. 3,658,051 discloses the application of a relatively strong electromagnetic pulse to ailing parts of a body, each pulse having a duration of approximately a quarter second, with a frequency of approximately two pulses per second, such pulsating magnetic field being applied to such body for a period of a few minutes. These pulses are administered to certain specified sites, although there is no suggestion that the electromagnetic radiation be applied to acupuncture points or any other nerves in a body.

Basically, the ancient Chinese art of acupuncture works on the theory and principal that the placement and positioning of acupuncture needles in specified locations on the body blocks the path of neurological transmission of pain impulses thereby relieving a patient of certain pains. In addition, the placement of such needles in acupuncture points or trigger points can be used to initiate certain nerve impulses thereby ennervating various internal glands and organs to activation. As a second step to the approach of applying needles to the specified acupuncture points, a variation which has recently been used, and is described in some of the patents listed above, is the use of acupuncture needles providing a low level electrical stimulation at the acupuncture points thereby, in theory, providing an accentuated stimulus at said points.

Another method for treatment of certain muscle and joint related bodily pains, which method is well-known in the western world, comprises application of heat such as using a heating pad or whirlpool of hot or warm water to the joints. However, there has not heretofore been a combination of acupuncture and such western medical techniques such as heating pads or physical therapy to benefit patients having various aches, pains and the like such as those caused by arthritis, rheumatism, osteoarthritis, gout, migraine, gonarthritis, newralgia, lumbargo and similar muscle and joint problems. Moreover, some persons, particularly westerners, have been somewhat reluctant to undergo acupuncture treatment as a result of their fear of the acupuncture needles. In addition, the use of acupuncture needles which are inserted into a patient's body carry a risk of transmitting disease from one patient to another, since the needles are typically reused. The present invention seeks to overcome some of the problems with the old acupuncture to provide such treatment in a manner somewhat more acceptable to westerners, and which provides a broader range of treatment for many ailments.

SUMMARY OF THE INVENTION

The present invention comprises a device which simulates an acupuncture needle without any insertion of such needle into a patient. In place of the needle, an electromagnetic pulse having a frequency of 2 to 16 hertz, which electromagnetic pulse is applied to an acupuncture point for about 20 to 30 minutes in the same way a needle is used in conventional acupuncture therapy.

In addition to the benefits provided by the application of the electromagnetic energy to the acupuncture point, the invention also provides electromagnetic stimulation of a muscle at a proper rate which has been shown here to relieve muscle tension and reduce the general aches and pains associated therewith.

The present invention comprises an oscillating means for electronically oscillating an electrical signal in the range of 2 to 16 hertz, a power supply for supplying an electric current to said oscillating means, and an electromagnetic producer means connected thereto for producing low power electromagnetic radiation pulses. The device also contains two regulators, one regulator being connected to the oscillator means for increasing the oscillation of the electrical signal within the range of 2 hertz to 16 hertz, the frequency thereof being proportional to the depth of penetration of the electromagnetic radiation pulses. A second regulator controls the strength of the electromagnetic radiation, by controlling the voltage applied to the pulse emitter, preferably in the range of 0.0 to 0.032 Joules per second. The electromagnetic producer means comprises a pair of coils in series, each coil having windings in one direction, and then in the opposite direction with a ratio of the number of turns in one direction to the opposite direction being approximately 10 to 1. One of the coils is oriented with magnetic north and the second coil is oriented with magnetic south facing in the same direction. The small number of windings in the opposite direction on each coil directs the magnetic field outward along the axis of the coil.

In the operation of the present invention, the device is placed at an acupuncture points, which such points are well known in the art. The device is activated and the frequency of the electromagnetic pulse is set in accordance with the treating physicians determination as to the required depth of penetration, as such doctor would similarly determine the depth to which an acupuncture needle should be inserted. Similarly, the desired amount of energy is set in accordance with a doctor's determination of the desired intensity of electromagnetic radiation.

The stimulation of the acupuncture point when the pulses reach the acupuncture point for 20 to 30 minutes blocks the nerve impulses through that area thereby preventing pains causes by such diseases as arthritis, rheumatism, osteoarthritis, gaut, migraine, gonarthritis, neuralgia, lombargo and similar such disorders. Moreover, since there is no actual needle penetration, patients who are generally afraid of the sight of such needles, and more importantly the penetration of such needles into their body, particularly in consideration of the fact that generally acupuncture needles are approximately five inches long, are relieved from the anxiety caused thereby.

In addition to the acupuncture effect of the present invention, the application of electromagnetic radiation causes a stimulation of the muscle to which such electromagnetic radiation is applied at a preselected frequency to mildly and gently heat such muscle as a result of the application of electromagnetic radiation thereby relaxing the muscle.

BRIEF DESCRIPTION OF THE DRAWINGS

FIG. 1 shows a top partially cut-away view of the hand unit of the present invention.

FIG. 2 is a side partially cut-away view of the hand unit of the present invention taken through lines 2—2 of FIG. 1.

FIG. 3 is an end sectional view of the present invention taken through lines 3—3 of FIG. 2.

FIG. 5 is a schematic drawing of one coil.

DETAILED DESCRIPTION

Figure 4:
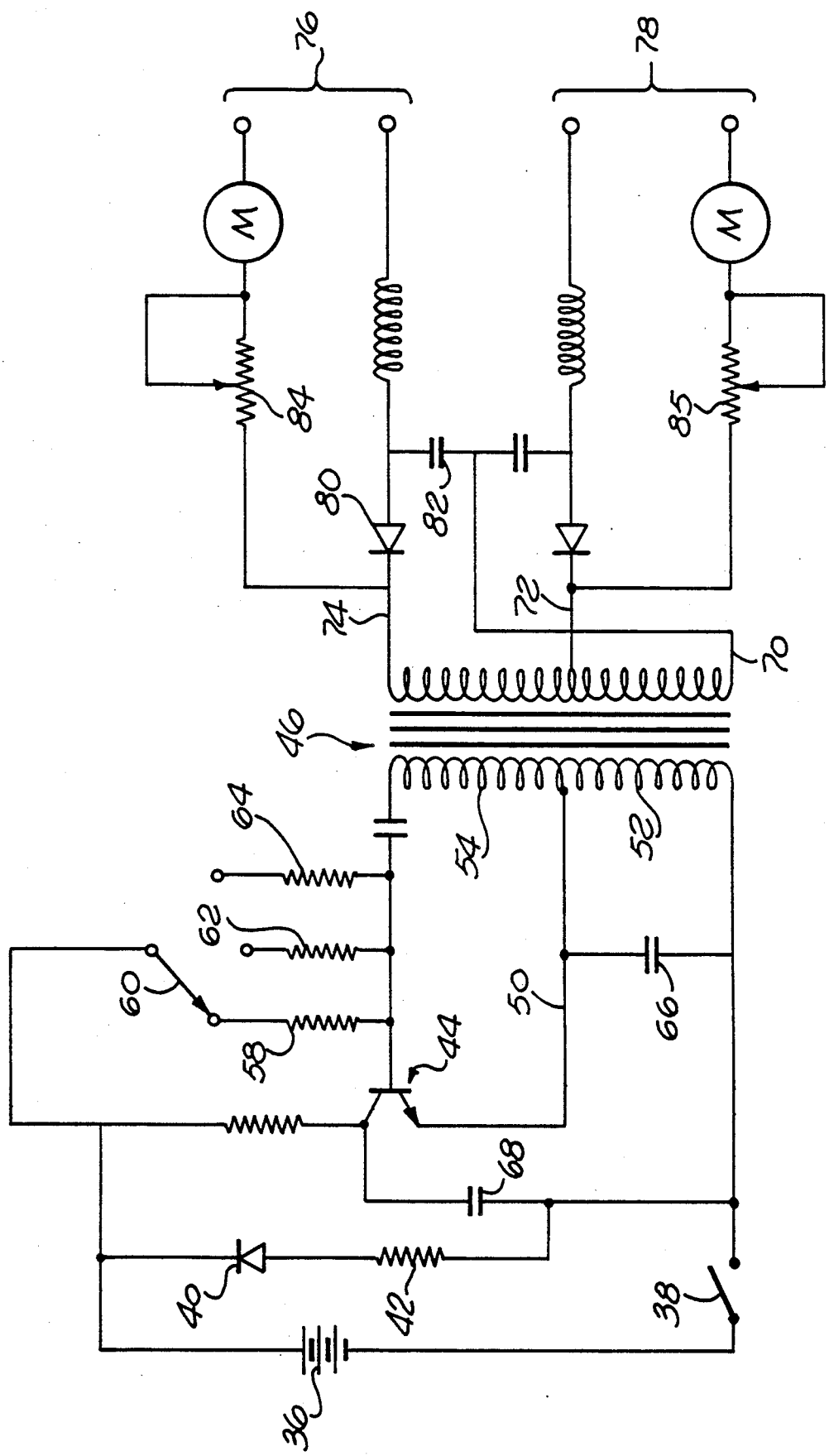
FIG. 4 is schematic diagram of the present invention.

Now referring to FIGS. 1 through 3, a top view and side and end views partially cut away of the hand unit containing the transducers assembly may be seen. The hand unit is comprised of a molded plastic housing 20 supporting a pair of transducers 22 and 24 and supporting an energy level control 26. The transducers 22 and 24 are nickel plated brass members each comprised of an upper cylindrical section having integral therewith at the lower end thereof a shaped pole-like member having a diameter of approximately one-half inch. These members are encapsulated in a resin 28 with a center line spacing of preferably approximately 11/16th of an inch so as to project downward from the housing for convenient positioning against parts of the body to be treated.

Each of these two transducers have windings thereon to provide a magnetic field aligned with the transducer in response to the current in the coil thereon. The preferred embodiment the coils on each of the two transducers are connected in series with the two windings being connected with an opposite winding sense so as to encourage at least part of the magnetic field generated by each to link the other. The windings, however, are of an unequal number of turns, in the preferred embodiment one winding being one hundred turns and the other winding being ten turns of magnet wire. The unequal number of turns help provide the desired field shape for penetration purposes by eliminating the extent of the linkage of the field from one transducer to the other which would tend to confine the field to the transducers without significant body penetration.

FIG. 5 is a schematic drawing of one embodiment of a transducer coil 90. As illustrated, there are 9 windings 91 in one direction D1 and one winding 92 in the opposite direction D2. When an electric curing is passed through the coil, the windings 91 create a magnetic field forming a North pole N1 and a South pole S1, and winding 92 creates a magnetic field having a North pole N2 and South pole S2 in the opposing direction along the same axis. This configuration creates a magnetic field with the desired field shape. As one skilled in the art will recognize, any number of windings having a similar 10:1 ratio will create a similarly shaped magnetic field.

The two coils 30 and 32 connected together as hereinbefore described are in turn connected in series with a potentiometer supported on housing 20 transforming the energy level control 26 shown in the figures, with the overall series combination being connected to a pair of leads 34 through the end of housing 20 for connection to the power source shown in detail in FIG. 4. The power source is a separate unit designed either for battery operation as in the embodiment shown or for operation from normal AC power. The circuit shown is driven by battery 36 coupled in circuit by on/off switch 38. With switch 38 on, power is applied to the light emitting diode 40 to indicate the on condition, the current through the diode being limited by current limiting resistor 42. Power is also applied to an oscillator comprising in part the transistor generally indicated by the numeral 44 and the primary of the transformer generally indicated by numeral 46. In particular, when the base of transister 44 has a voltage of at least 7/10ths of a volt above that of the emitter thereof, the transistor will be turned on whereby power is delivered from the battery through resistor 48 to line 50 thereby providing a voltage drive on the lower part 52 of the primary of the coil. The changes in the flux in the coil of the transformer during operation of the oscillator generate a feedback voltage in the upper part 54 of the transformer primary to provide a feedback to the base of transistor 44, to control, the on/off condition thereof depending upon the phase shift resulting from the combination of capacitor 56 and resistor 58. Switch 60 allows for the selection of either of resistors 62 and 64 thereby changing the phase of the feedback and adjusting the frequency accordingly. In the preferred embodiment these resistors are selected to provide a selection of frequencies ranging from a low of 2 Hertz to a high of 16 Hertz. It is believed that the frequency essentially affects the penetration level to provide for the stimulation of the desired acupuncture point. During the transistor off periods, capacitor 66 completes the oscillator circuit with coil 52, with capacitor 68 being charged through resistor 48 during the transistor off periods to provide some storage of charge to aid in the supply of power to the transistor when the transistor is turned on again.

The secondary period of transformer 46 in the embodiment shown also has three leads thereon, specifically leads 70, 72 and 74. Lead 70 effectively serves as a common with lead 72 and 74 providing two different AC voltage levels with respect thereto. In that regard, the circuit shown in FIG. 4 provides two output energy levels depending on whether leads 34 of the hand unit are plugged into terminal lines 76 or 78 of the circuit of FIG. 4. Referring for the moment to the circuit connected to lead 74 the secondary, it will be noted that diode 80 and capacitor 82 are connected in series between the effective common lead 70 and lead 74. Thus, during the part of the cycle of the oscillator wherein the voltage on lead 74 is negative with respect to lead 70, capacitor 82 will be charged through diode 80 with the relatively low voltage drop across diode 80 during such charging appearing as the output 76 of the circuit. During the opposite half cycle, however, diode 80 is back biased so that current will flow through potentiometer 84 and meter 86, through the transducers and then back through capacitor 82 tending to discharge the capacitor and recharge it with opposite polarity. In that regard, meter 86 provides a quantitative measure of the energy being delivered with potentiometer 84 providing an adjustment of that energy in the same manner as the energy level control 26 on the hand unit itself. Thus, the circuit delivers to the hand unit a train of current pulses adjustable in level both at the power supply and at the hand unit, and at an adjustable frequency, the circuit delivered to lead 72 of the transformer secondary to provide output 78 functions in the same manner as that for providing output 76 though being connected to a lower voltage tap on the secondary will deliver a lower power range of current pulses to the hand unit. Of course, these circuits may readily be replicated to provide power to additional transducer assemblies as desired. Obviously, of course, the use of adjustment 84 and/or meter 86 is not essential to the operation of the system and may be eliminated if cost is an overriding factor.

In another embodiment of the present invention, a base unit is provided with transformer and oscillation circuitry, and control systems for regulating the frequency and intensity of the electromagnetic pulses, with only transducers disposed remote from the base unit and electrically connected thereto. A plurality of pairs of transducers are provided for placement on a plurality of acupuncture points simultaneously.

METHOD OF USE

To use the above-described apparatus, the user must first be skilled, or informed, in the art of acupuncture so that he can provide to a patient electromagnetic stimulation at the acupuncture points, also known as trigger points. In this connection, a number of books have been written and are available in the prior art depicting the various acupuncture points, which have been known for thousands of years by the ancient Chinese as a standard part of their regular medical practice. In theory, acupuncture points are emperically and philosophically derived specified sites on a body which when perturbed, by the insertion of a specialized stainless steel acupuncture needle or otherwise, would modify the flow of nerve impulses through the body so as to block nerve impulses from certain areas of a patient's body which are in pain or are otherwise ailing. For example, for the treatment of abdominal pain, it has been long recognized that the insertion of a needle approximately three inches below the kneecap and one inch lateral to the tibia, and the insertion of a second needle approximately four inches above the navel along the midline of the abdominal surface can be employed to relieve such pain. As another example, for the treatment of asthma, needles have routinely been inserted in four positions, namely, one needle applied approximately four inches above the navel along the midline of the abdominal surface, a second needle being applied approximately one inch lateral to the lower end of the seventh cervical disk, a third needle applied to approximately 1.5 inches lateral to the lower end of the third thoracic disk, and a fourth needle applied approximately three inches lateral to the lower end of the fourth thoracic disk. Many other treatments have been worked out for the various ailments as a result of thousands of years of medical research by the ancient Chinese performing empirical studies on the effect of acupuncture. However, as described above, now that the ancient Chinese art of acupuncture has come to the western world and is being practiced here, a number of changes, adaptations and modifications are being made to the ancient techniques, in part to make them more acceptable to western society. One problem, in particular, is the fact that many westerners look with unfavorable consideration upon the placement in, or near their body, of sharp and stainless steel needles approximately five inches long. Thus, the present invention provides a noninvasive method of obtaining the same effect as the ancient art of Chinese acupuncture, without any of the disadvantages with respect to the insertion of needles in the patient. In combination with this benefit, is the general benefit, which has been found to occur when the human body is subject to electromagnetic radiation. Nevertheless, none of the above-noted references in any suggest or disclose the application of low frequency, low power electromagnetic pulses applied directly to acupuncture sites for the purpose of stimulating muscle contractions thereby relaxing the muscles as one would do for physical therapy.

With this in mind, the doctor, or acupuncturist, first locates the acupuncture point or points, precisely, to which the electromagnetic radiation is to applied. Once these acupuncture points are located, the doctor must make a determination with respect to the required depth of penetration of the electromagnetic pulse and the intensity thereof. The depth of penetration is determined by a skilled acupuncturist depending upon the desired intensity of reaction for a particular patient in the same way as such acupuncturist would determine the depth to which a needle should be placed in the conventional use of an acupuncture needle. Thus, this determination can be made and is well within the skill of one of ordinary skill in the art of acupuncture. In general, the depth of penetration is selected by a determination of the desired intensity of the patient's reaction to the acupuncture treatment. For example, if a joint is particularly stiff or sore, vigorous or strong stimulation resulting in a large movement of the joint would generally not be beneficial to a patient, but instead, a milder treatment (i.e. less penetrating pulse) would typically be used to avoid excess trauma to the patient. Of course, the actual extent and desirability of deeper penetration would be within the discretion of the treating physician based upon a determination made with the consideration of a large number of medical facts relating to the ailment as well as the patient. The treatment of a patient with higher frequency electromagnetic radiation causes a deeper penetration than lower frequency pulses. In addition to the frequency adjustment, which can either be stepped, or continuous, depending upon the particular arrangement of the oscillator circuit, in the range of 2 to 16 hertz, the intensity of the electromagnetic radiation can also be controlled by a coincident increase or decrease of the voltage of the device. The use of greater intensity electromagnetic energy produce a stronger, faster reaction to the treatment, which can also be gauged by a skilled acupuncturist.

After the acupuncture points are selected in accordance with general acupuncture techniques which are known in the art, in accordance with the problem or pain of which the patient complains, the machine is turned on and the transducers are placed against the preselected acupuncture point. The energy control, which controls the voltage which, in turn, controls the strength of the electromagnetic field, is gradually increased so that the user can feel the electromagnetic pulses pulsing at the acupuncture site point. This energy control level is increased to a desired level. The acupuncture point is then pulsed for approximately 20 to 30 minutes, and sometimes as long as 40 minutes to provide a single acupuncture treatment. Each such treatment is repeated as often as necessary until the patient achieves the desired relief.

CASE STUDIES

A hundred and fifty case experiences were obtained by a licensed, skilled acupuncturist physician with the following etiology and results. The patients were broken down into four groups based upon their particular ailments. Group A, consisting of 60 patients, had myositis pain syndrome. Group B, consisting of 50 patients, complained of tension headache, sinus headache and stiff neck. Group C, consisting of 30 patients, complained of stomach pain, either chronic or spasm. Group D, consisting of 10 patients, complained of dizziness and did not exhibit any clear ediology.

Of the Group A patients, 95 percent of the patients were symptom free after 25 to 30 minute treatments three times per week for one month. Of the Group B patients, 85 to 90 percent experienced instant relief or marked improvement in their symptoms with 30 minute treatments, three times per week for one month. Of the Group C patients, all patients enjoyed relief of the exhibited pain after usually 30 minutes of treatment, three times per week. Of the Group D patients, 70 to 80 percent of the patients complained of fewer dizzy spells as a result of 40 minutes of treatment three times per week for two months.

Thus it can be seen that the present invention appears to have the same affect as other forms of acupuncture treatment using needles without any of the concommitent pain or anxiety resulting from the placement of needles in a body. Applicant has disclosed herein the preferred embodiment of the present invention; however, it will be apparent to one of ordinary skill in the art that many modifications and substitutions of the various components described herein can be obtained without departing from the spirit and scope of the present invention. Therefore, Applicant's invention is limited solely by the scope of the claims, and the reasonable equivalents thereof, and not by the detailed description as specified herein.

Wherefore, I claim:

1. An electromagnetic energy pulse emitter for the stimulation of acupuncture points comprising:
   means for providing pulses of electric current at a frequency in the range of 2 to 16 hertz;
   transducer means, comprising a plurality of coils in series, responsive to said electric current pulses by emitting electromagnetic radiation pulses at the same frequency;
   said plurality of coils having a pair of coils connected to each other in series, disposed adjacent one another and aligned along a same axis so that a relatively linear magnetic pulse is provided;
   said coils are pulsed with an electric current forming an electromagnet having a north end and a south end; and said north end of the one of said coils is adjacent said south end of the other of said coils; and
   each of said coils comprising a first having approximately 10 times the number of windings as a second coil.

2. An electromagnetic pulse emitter simulating the activity of acupuncture needles with respect to the stimulation of acupuncture points comprising:
   an oscillating electric current source for providing low level electric current in the frequency range of 2 to 16 hertz;
   an adjustable frequency means for adjusting the frequency range of said oscillating current to a predetermined frequency in the range of 2 to 16 hertz;
   transducer means for converting said oscillating electric current to a magnetic pulse at the same frequency as said electric current;
   said transducer means comprising a plurality of pairs of coils, each coil in said pair of coils being wound a first number of windings in a first direction, and then a second number of windings in a second direction, the first number of windings being approximately ten times the second number of windings;
   a housing for containing each pair of coils, said housing adapted to be hand-held; and
   energy control means in series with said transducer means and disposed on said housing for controlling the strength of the magnetic field produced by said transducers.

* * * * *